(12) United States Patent
Kats

(10) Patent No.: US 7,345,291 B2
(45) Date of Patent: Mar. 18, 2008

(54) DEVICE FOR IRRADIATION THERAPY WITH CHARGED PARTICLES

(75) Inventor: Mark Kats, Moscow (RU)

(73) Assignee: Ion Beam Applications S.A., Louvain-La-Neuve (BE)

( * ) Notice: Subject to any disclaimer, the term of this patent is extended or adjusted under 35 U.S.C. 154(b) by 17 days.

(21) Appl. No.: 10/512,772

(22) PCT Filed: Apr. 30, 2003

(86) PCT No.: PCT/BE03/00079

§ 371 (c)(1),
(2), (4) Date: Jan. 9, 2006

(87) PCT Pub. No.: WO03/092812

PCT Pub. Date: Nov. 13, 2003

(65) Prior Publication Data

US 2006/0106301 A1    May 18, 2006

(30) Foreign Application Priority Data

May 3, 2002   (EP) .................................. 02447078

(51) Int. Cl.
*A61N 5/10* (2006.01)
*A61N 5/00* (2006.01)
*G21G 5/00* (2006.01)

(52) U.S. Cl. ............................. 250/492.22; 250/492.1; 250/492.21; 250/492.3; 378/65; 378/68; 378/69

(58) Field of Classification Search ............ 250/492.22
See application file for complete search history.

(56) References Cited

U.S. PATENT DOCUMENTS

| | | | |
|---|---|---|---|
| 4,101,120 A * | 7/1978 | Seshima | .......................... 5/616 |
| 6,265,837 B1 * | 7/2001 | Akiyama et al. | ............ 315/503 |
| 6,433,349 B2 * | 8/2002 | Akiyama et al. | ......... 250/505.1 |
| 6,449,336 B2 * | 9/2002 | Kim et al. | ...................... 378/65 |
| 6,476,403 B1 * | 11/2002 | Dolinskii et al. | ......... 250/492.3 |
| 6,615,429 B2 * | 9/2003 | Weil et al. | ...................... 5/601 |
| 6,635,882 B1 * | 10/2003 | Pavlovic et al. | ............. 250/398 |
| 6,717,162 B1 * | 4/2004 | Jongen | ..................... 250/505.1 |
| 6,730,921 B2 * | 5/2004 | Kraft | ........................ 250/492.1 |
| 6,904,125 B2 * | 6/2005 | Van Dyk et al. | ............... 378/65 |
| 2002/0030164 A1 * | 3/2002 | Akiyama et al. | ......... 250/492.1 |
| 2006/0106301 A1 * | 5/2006 | Kats | ............................ 600/415 |

FOREIGN PATENT DOCUMENTS

| | | |
|---|---|---|
| DE | 100 10 523 A1 | 9/2001 |
| DE | WO 01/66187 A1 * | 9/2001 |
| EP | 0 864 337 A2 | 9/1998 |
| EP | 1 121 957 A2 | 8/2001 |

* cited by examiner

*Primary Examiner*—David A. Vanore
*Assistant Examiner*—Bernard Souw
(74) *Attorney, Agent, or Firm*—Fitch, Even, Tabin & Flannery

(57) ABSTRACT

The present invention is related to a device for irradiating a patient with a charged particle beam, comprising a number of beam channels attached to a vertical wall, wherein a deflection magnet is present at the end of each channel. This deflection magnet is able to deflect the beam in the vertical plane over a given angle range. The couch whereon the patient is reclining is mobile in the vertical plane, so that the combined movement of the patient, and the variable deflection of the beam allow one point in the patient to be irradiated from several angles in the vertical plane.

9 Claims, 2 Drawing Sheets

DEVICE FOR IRRADIATION THERAPY WITH CHARGED PARTICLES

FIELD OF THE INVENTION

The present invention is related to a device for directing a beam of charged particles to a target from several different angles during irradiation. A device like this is often referred to as a 'Gantry'.

STATE OF THE ART

A known device for directing a charged particle beam from several different angles is a rotating gantry, such as the one described in document U.S. Pat. No. 4,917,344. This type of device comprises a large barrel or squirrel-cage structure, on which magnets are mounted for directing the beam along the axis of rotation, away from it, and back again towards the isocentre, located on the rotation axis. By combining a $2\pi$ rotation of the gantry around a horizontal rotation axis with a $2\pi$ rotation of the target around a vertical axis, one can irradiate the target from any direction, i.e. from a full sphere ($4\pi$ solid angle). In order to achieve a good precision in the direction of the beam, the requirements on the mechanical structure in terms of rigidity and precision are very high. The total weight of the rotating structure, including the magnets, may be as high as 100 T. The rotating structure may be as large as 10 m in diameter and 10 m in length, leading to an excessive cost of such a proton or heavy ion therapy system.

It has therefore been proposed to achieve the same goal by replacing the rotating structure by a set of different beam lines in a vertical plane. A number of fixed beam lines does not allow to irradiate the target from any direction. Several solutions have been proposed to add some flexibility to a set of fixed beam lines. The most recent prior art in this domain can be found in the article entitled "Planar system replacing gantry for protons and carbon ions beams transportation", M. M. Kats, Proceedings of the Sixth European Particle Accelerator Conference (EPAC'98), pages 2362-2364.

This document describes two versions of a planar magnetic optic system for transportation to the patient of a proton or carbon ion beam from various directions. The beam is bent, focused and directed towards an isocentre in one of a plurality of magnetic channels which are fixed immovably on a vertical wall. The patient is placed at the isocentre. Two additional magnets are used to change the irradiation direction, said magnets being either mobile or immobile. In the mobile magnet version, the magnets are attached to a rotating frame. Even though its weight is inferior to that of a rotating gantry, this is still a complex mechanical structure. Alternatively, the above cited document suggests the use of two large and semi-circular magnets, or of a plurality of sector magnets. These magnets are however unacceptably large and heavy. In all cases, the last two magnets of a particular beam line are used for the deflection of the beam, so that irradiation on the stationary patient is performed from a large range of angles. All of the existing systems are based on the principle of isocentricity, i.e. they aim at irradiating a fixed point in the patient from a plurality of angles. To irradiate a zone around this point, sweeping magnets are added, which scan the beam over a given area at each angular position.

Document DE-A-10010523, describes a system with multiple treatment rooms, each room being equipped with one channel for producing a beam. One particular embodiment mentions a system comprising three rooms, two of which having a channel wherein the beam can be deflected over an angle between −15° and +15°. In another room, the beam can be deflected over an angle between −30° and +30°. In each room, the patient is in a horizontal position and can be moved along a vertical line, to obtain different angles of incidence for different deflections. The patient can also be rotated around the vertical axis, in order to irradiate from every angle in the horizontal plane. Within one treatment room, given the limited range of deflection angles, the range of irradiation angles with respect to the patient is equally limited, hence the need for multiple rooms.

Equally in document DE-A-10010523, sweeping (also called scanning) magnets may be present in the beam channels, said sweeping magnets being positioned after the deflection magnets. This position requires the sweeping magnets however to move along with the deflection of the beam, necessitating a rather complex technical design.

AIMS OF THE INVENTION

The present invention aims to provide a planar irradiation device for particle beam therapy, which works with lightweight magnets, and allows an irradiation of a zone in the patient from any angle in a continuous range, without the need of an expensive and complex high-precision rotating device.

SUMMARY OF THE INVENTION

The present invention is related to a device for irradiating a patient by a charged particle beam, said device comprising a plurity beam channels, which are to be connected to a beam source, said channels being placed in a fixed way in a vertical plane, characterised in that one deflecting magnet is present at the end of each channel, said magnet being able to deflect the beam over a deflection angle in said vertical plane, the device comprises a patient positioning system, comprising means to move the patient in said vertical plane.

In the preferred embodiment of the invention, said angle of deflection is variable within a predefined range, and said patient positioning system comprises means to move the patient in such a way that the same point within the patient is irradiated by a beam produced by said channel, for different values of said deflection angle. In the preferred embodiment, said patient positioning system comprises means to move the patient in all directions in a vertical plane.

The channels are preferably attached to a vertical wall.

According to one embodiment, each of said channels further comprises at least one sweeping magnet, for irradiating an area around said point. According to the preferred embodiment, said at least one sweeping magnet is in a fixed position and located—starting from said beam source—before said deflecting magnet.

Said patient positioning system preferably comprises means for rotating said patient around a vertical axis.

According to some preferred but non-restricitive embodiments, the device of the invention may comprise five channels three channels.

SHORT DESCRIPTION OF THE DRAWINGS

DETAILED DESCRIPTION OF THE INVENTION

Figure 1:
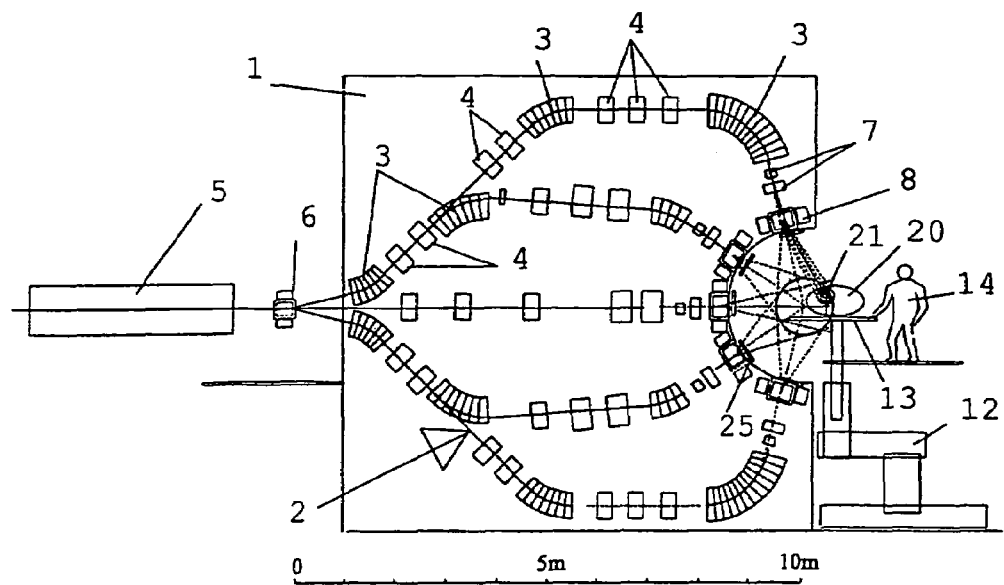
FIG. 1 represents a device according to a first embodiment of the invention.
Figure 2:
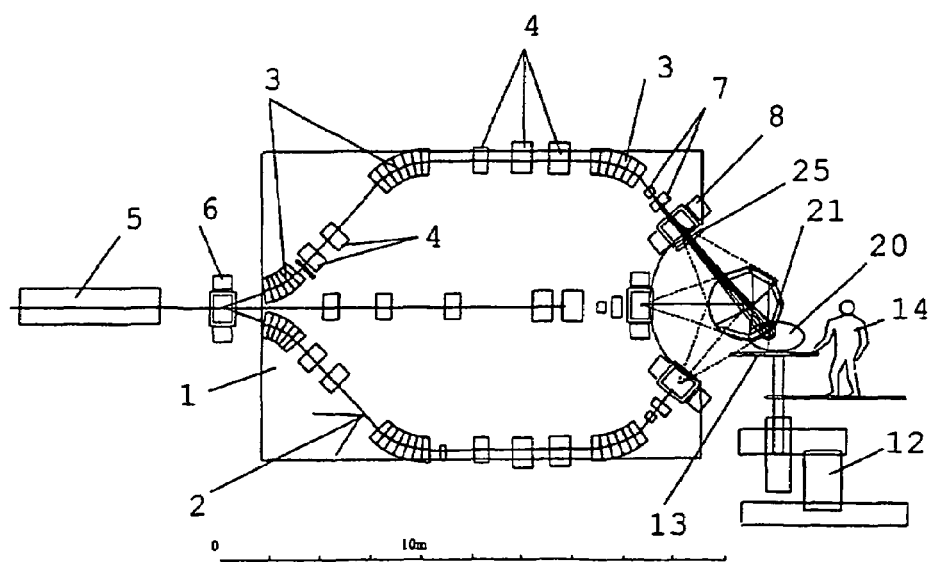
FIG. 2 represents a device according to a second embodiment of the invention.

As seen in FIG. 1, the device according to the invention comprises a plurality of fixed magnetic channels 2, in a vertical plane, preferably fastened to a vertical wall 1. A channel is defined as a sequence of magnets and lenses, which force a particle beam onto a predefined path, in the plane of the vertical wall. In the case of FIG. 1, five channels are present, but this number may differ within the scope of the present invention. FIG. 2 shows a variant comprising three channels. In the figures shown, the patient 20 is in a reclining position, lying on a couch 13.

Each channel comprises a number of deflecting magnets 3 and lenses 4. The beam is produced by a common source, which is a known particle accelerator 5, for example a cyclotron, and a beam transport system. One deflecting magnet 6 is common to all channels, and provides the first deflection in the direction of one of the channels present. In the embodiment with five channels, two adjacent channels may have a number of magnets and lenses, which are common to both channels. In both embodiments, beam monitors 25 are present at the end of all or a part of the channels. Their function is to measure beam position and/or current.

In the embodiments of FIGS. 1 and 2, two sweeping magnets 7 (Swx, Swy) are present in each channel for scanning the beam in two directions (x,y) perpendicular to the beam direction, over a given area 21. At the end of each channel, a single deflecting magnet 8 is present, which allows a deflection of the beam over a fixed and predefined angle, with respect to the non-deflected beam direction 9 of said channel (see detail FIG. 3). The deflection is such that the beam remains in the vertical plane of the wall.

Figure 3:
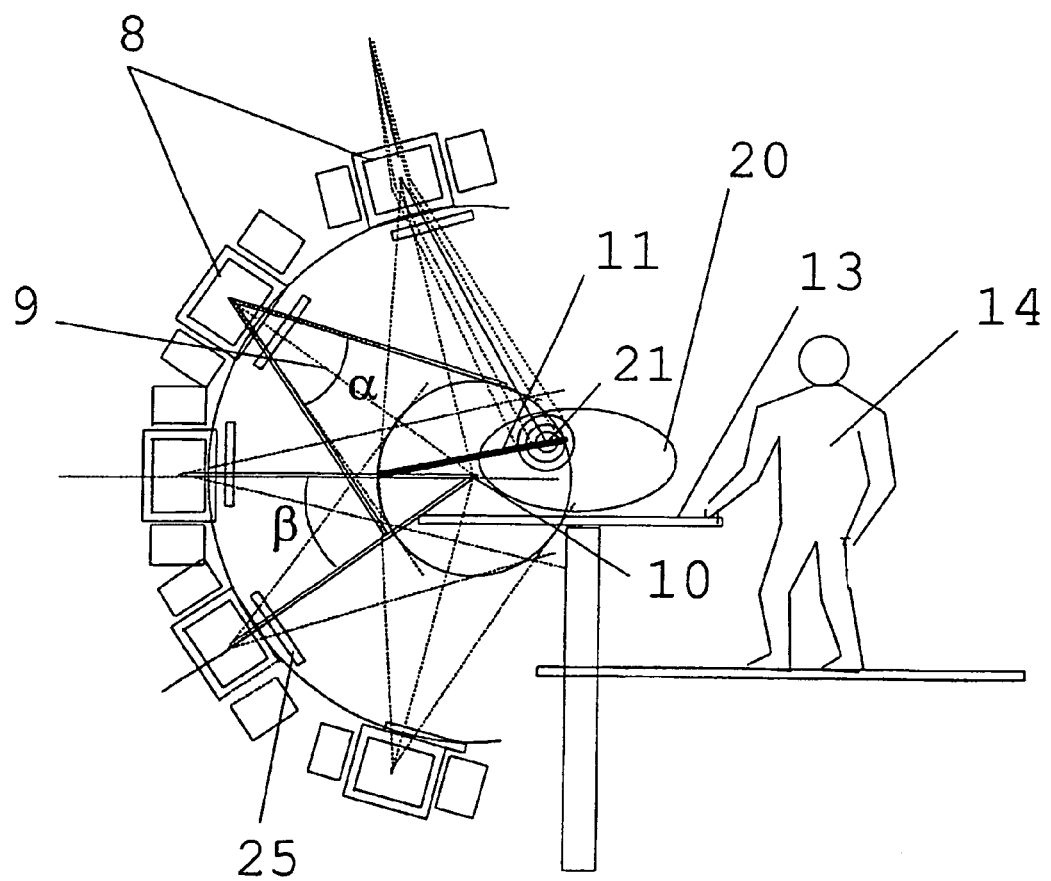
FIG. 3 represents a detailed view of the angular ranges of the deflecting magnets used in the present invention.

The maximum range $\alpha$ of deflection angles for a given deflecting magnet 8 is preferably equal or larger than the angular distance $\beta$ between two neighbouring channels as seen from a point 10, as is illustrated in the detail in FIG. 3. In that case, the angular ranges for each beam line are contiguous or overlap. The angle $\alpha$ may also be less than the angle $\beta$, in which case there is a gap between the angular ranges of two successive beam lines. The angular distance $\beta$ between two successive beam lines need not be constant. Also it is not required that the maximum ranges a of deflection angles for each beam line be equal. In the drawings, the point 10 is shown as the isocentre of the different channels, i.e. the point which is common to the beams produced by all channels 2, in the absence of any deflection by the end magnets 8. However, it should be made clear that the presence of such an isocentre is not necessary according to the invention, as will be made clear in the next paragraph.

Contrary to existing devices, the device of the invention is not isocentric. If the patient would remain stationary, the changing of the deflection angle of the top channel beam would cause the irradiation of a line 11 of points, instead of a fixed point. The same is true for the other channels. In order therefore to irradiate a given point in the patient, the couch on which the patient is reclining, is movable in all directions in the vertical plane. A suitable horizontal and/or vertical movement of the couch, combined with the changing of the deflection angle within the range $\alpha$, allows the beam to remain directed at a fixed point within the patient.

The movement in any direction in the vertical plane allows the distance between the deflection magnet and the target to remain constant during irradiation from different angles, which is not the case in prior art systems wherein the patient is moved only along a straight, vertical line.

The sweeping magnets 7 allow the irradiation of a predefined area 21 around the point in question. According to the preferred embodiment of the invention, the sweeping magnets 7 are placed in a fixed position in the beam line before the deflection magnets 8 (starting from the source), as can be seen in FIGS. 1 to 3. This position of the sweeping magnets allows them to be installed in a stationary position with respect to the deflection magnets, for all values of the deflection angle.

The couch 13 is installed on a patient positioning system or PPS 12. In the preferred case, the patient 20 is in a reclining position on this couch. A system wherein the patient is seated may also be used, especially when using a horizontal beam line. The PPS comprises means to move the couch in the vertical plane. A person 14 attending to the patient must have easy access to the couch or seat.

The patient positioning system further has the ability to rotate the patient around a vertical axis, passing trough the target centre, in order to irradiate the patient from the full range of angles 0-360° in the horizontal plane.

Before the treatment, the therapist defines a fraction, i.e. the irradiation applied during one session, as being one or more fields. A field is the irradiation of one target volume from one direction. For applying a field, the required beam line is selected, the current fed to the deflecting magnet 8 is adjusted for obtaining the required fixed deflection angle, the PPS is moved so that the target lies in the beam direction, and the irradiation for the first field is applied. This procedure is repeated for all fields in the fraction.

For applying the irradiation to a volume around the target centre, the so-called "pencil-beam scanning" may be used. In the "pencil-beam scanning", the sweeping magnets Swx and Swy are driven with such currents that a narrow beam moves on a path on an area around the target centre. The depth of said area is then varied by changing the energy of the beam particles, with an energy degrader. This procedure is repeated until the whole volume of the field receives the prescribed irradiation dose.

In the embodiment of FIG. 1, the full range of 0-360° can be obtained in the horizontal and in the vertical plane. In the embodiment of FIG. 2, a range of [−70°,+70°] is obtained in the vertical plane on both sides of the patient.

According to another embodiment of the invention, no sweeping magnet 7 (Swx) for scanning in the plane of wall 1 is present, and the scanning of the area to be treated is done by the changing of the deflection angle (in the range $\alpha$) itself. A single sweeping magnet 7 (Swy), preferably placed before the deflection magnet, is used for scanning in the direction perpendicular to the plane of the wall.

Compared to the prior art, the device of the invention having a plurality of beam channels, provides—within one treatment room—a larger range of irradiation angles with respect to the patient, compared to the system wherein one beam channel is applied. The multi-channel embodiment makes it unnecessary to devise a system having multiple treatment rooms, each equipped with a single beam channel.

DESCRIPTION OF A PREFERRED EMBODIMENT OF THE INVENTION

The two embodiments shown in the FIGS. 1 and 2 will now be described in more detail. In FIG. 1, a five-channel device is shown. It comprises a vertical wall of 9 m in width and 8.5 m in height. The maximum deflection angle range α for each end deflecting magnet 8 is 30° (between +15° or −15° from the non-deflected line). Movement of the patient couch over a distance of maximum about 0.5 m (i.e. inside a sphere centred at the intersection of the multiple undeflected beam lines, and having a radius of 0.5 m) is combined with this deflection in order to irradiate from a continuous range between −90° and +90° in the vertical plane on one side of the patient, so a continuous 0-360° range can be obtained by rotating the couch around the vertical axis. Sweeping magnets allow two-directional scanning (x and y) over a target area with a maximum diameter of 0.3 m. The Source-axis distance (scanning magnets to irradiated point) SAD is 3 m.

The device of FIG. 2 is a three channel device, with a wall of 8 m in width and 6 m in height. α=40° (+ or −20° from the non-deflected line). Movement of the patient over a distance of maximum 0.7 m is combined with beam deflection in order to irradiate from a continuous range between −70° and +70° in the vertical plane on one side of the patient. The couch is rotatable over 0-360° in the horizontal plane, around the vertical axis which passes through the target centre. Again, sweeping magnets allow two-directional scanning (x and y) over a target area with a maximum diameter of 0.3 m. The Source-axis distance (scanning magnets to irradiated point) SAD is 3 m.

The movements of the couch required for these two embodiments of the invention are easily attainable with PPS and couches or chairs known in the art, e.g. from U.S. Pat. No. 6,094,760.

The device according to the invention may be used for irradiating by any type of charged particles, such as protons, but is especially useful for heavy ion beams such as carbon or oxygen ion beams, which would require a very large and heavy structure in a rotating gantry.

The invention claimed is:

1. A device for irradiating a patient by a charged particle beam, said device comprising a plurality of beam channels each connected to a beam source, each of said channel being fixed in a vertical plane, said device further comprising:
   one deflecting magnet at the end of each channel, said magnet capable of deflecting the beam over a deflection angle in said vertical plane, and
   a patient positioning system, comprising means to move the patient in said vertical plane.

2. The device according to claim 1, wherein said angle of deflection is variable within a predefined range, and wherein said patient positioning system comprises means to move the patient in such way that the same point within the patient is irradiated by a beam produced by each of said channels, for different values of said deflection angle.

3. The device according to claim 2, wherein said patient positioning system comprises means to move the patient in all directions in a vertical plane.

4. The device according to claim 1, wherein each of said channels are attached to a vertical wall.

5. The device according to claim 4, wherein each of said channels further comprises at least one sweeping magnet for irradiating an area around said point.

6. The device according to claim 5, wherein said at least one sweeping magnet is in a fixed position and located before said deflecting magnet.

7. The device according to claim 1, wherein said patient positioning system comprises means for rotating said patient around a vertical axis.

8. The device according to claim 1, comprising five channels.

9. The device according to claim 1, comprising three channels.

* * * * *